US010677935B2

(12) United States Patent
Konkle et al.

(10) Patent No.: US 10,677,935 B2
(45) Date of Patent: Jun. 9, 2020

(54) LIGHT GUIDE LAYER FOR A RADIOGRAPHIC DEVICE

(71) Applicant: GENERAL ELECTRIC COMPANY, Schenectady, NY (US)

(72) Inventors: Nicholas Ryan Konkle, Waukesha, WI (US); Marc Schaepkens, Clifton Park, NY (US); German Guillermo Vera, Menomonee Falls, WI (US); Biju Jacob, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 289 days.

(21) Appl. No.: 15/396,660

(22) Filed: Dec. 31, 2016

(65) Prior Publication Data

US 2018/0188385 A1    Jul. 5, 2018

(51) Int. Cl.
G01T 1/20 (2006.01)
G01T 1/00 (2006.01)
G01T 1/24 (2006.01)
G01T 1/29 (2006.01)
A61B 6/00 (2006.01)

(52) U.S. Cl.
CPC .......... *G01T 1/003* (2013.01); *A61B 6/4233* (2013.01); *G01T 1/2002* (2013.01); *G01T 1/2018* (2013.01); *G01T 1/244* (2013.01); *G01T 1/2914* (2013.01)

(58) Field of Classification Search
CPC ..... G01T 1/003; G01T 1/2002; G01T 1/2018; G01T 1/244; G01T 1/2914; A61B 6/4233
USPC ............ 378/98.3, 98.8; 250/370.08, 370.09, 250/370.11
See application file for complete search history.

(56) References Cited

U.S. PATENT DOCUMENTS

| 5,059,800 | A | 10/1991 | Cueman et al. |
| 7,358,506 | B2 | 4/2008 | Daniel |
| 7,626,176 | B2 | 12/2009 | Zeitler et al. |
| 8,563,938 | B2 | 10/2013 | Konkle et al. |
| 2002/0079491 | A1* | 6/2002 | Raynor ............. H01L 27/14627 257/59 |
| 2008/0277588 | A1* | 11/2008 | Zeitler .................. G01T 1/202 250/370.11 |
| 2011/0248175 | A1* | 10/2011 | Frach .................... G01T 1/2018 250/363.03 |
| 2013/0249035 | A1 |  9/2013 | Hedler et al. |

(Continued)

FOREIGN PATENT DOCUMENTS

DE    10 2011 077195 A1    12/2012

OTHER PUBLICATIONS

Extended European Search Report and Opinion issued in connection with corresponding EP Application No. 17208007.9 dated Jun. 11, 2018.

*Primary Examiner* — Courtney D Thomas
(74) *Attorney, Agent, or Firm* — Fletcher Yoder, P.C.

(57) ABSTRACT

An x-ray detector, system and related method are described wherein a light redirection layer is provided and used to redirect light, converted from x-rays by a scintillator, to at least one pixel. The light redirection layer comprises at least one light redirecting cell comprising a channel and a light reflecting region, wherein the channel is arranged relative to the at least one pixel to direct the incoming light away from a non-light sensitive part of the at least one pixel and toward the light sensitive part of the at least one pixel.

19 Claims, 5 Drawing Sheets

(56) References Cited

U.S. PATENT DOCUMENTS

2014/0064446 A1   3/2014  Wear et al.
2016/0170296 A1*  6/2016  Wang ................ H01L 31/02327
                                                               430/5
2017/0307765 A1* 10/2017  Bures .................. G01N 23/046

* cited by examiner

LIGHT GUIDE LAYER FOR A RADIOGRAPHIC DEVICE

BACKGROUND

A number of radiological imaging systems of various designs are known. Radiological imaging systems generally are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes.

Many of the earlier radiographic imaging systems employ conventional X-ray imaging using film as the X-ray detection media. In order to obtain images from these systems, the imaging medium must be transported and processed after each exposure, resulting in a time delay in obtaining the desired images. Digital radiography provides an alternative that allows the acquisition of image data and reconstructed images on the spot for quicker viewing and diagnosis, and allows for images to be readily stored and transmitted to the viewing professional. These digital images displayed in digital form may not represent all of the x-rays that have passed through the subject of interest because some light, which was converted from the x-rays, is lost between the pixels. This creates a less precise image of the subject of interest and possible error.

BRIEF DESCRIPTION

In an embodiment, an x-ray detector comprises a scintillator configured to convert x-rays into light and a light redirection layer configured to redirect light from the scintillator to at least one pixel. The light redirection layer comprises at least one light redirecting cell comprising a channel and a light reflector region, the channel being arranged relative to the at least one pixel to direct incoming light away from a non-light sensitive part of the at least one pixel and toward the light sensitive part of the at least one pixel.

In another embodiment, a method for redirecting light comprises emitting x-rays from an x-ray source. The x-rays received by the scintillator are converted into light. The light is received into the light redirection layer and the light is redirected in the light redirecting layer using at least one light redirecting cell comprising a channel and a light reflective region, the channel being arranged relative to the at least on pixel to channel incoming light away from a non-light sensitive part of the at least one pixel and toward the light sensitive part of the at least one pixel.

In a further embodiment, an x-ray system comprises an x-ray source configured to generate x-rays and an x-ray receptor or detector. The receptor or detector comprises a scintillator configured to convert x-rays into light and a light redirection layer. The light redirection layer is configured to redirect light from the scintillator to at least one pixel. The light redirection layer comprises at least one light redirecting cell comprising a channel and a light reflecting region, the channel arranged relative to the at least one pixel to direct incoming light away from a non-light sensitive part of the at least one pixel and toward the light sensitive part of the at least one pixel.

DRAWINGS

The inventive subject matter described herein will be better understood from reading the following description of non-limiting embodiments, with reference to the attached drawings, wherein below:

DETAILED DESCRIPTION

Figure 1:
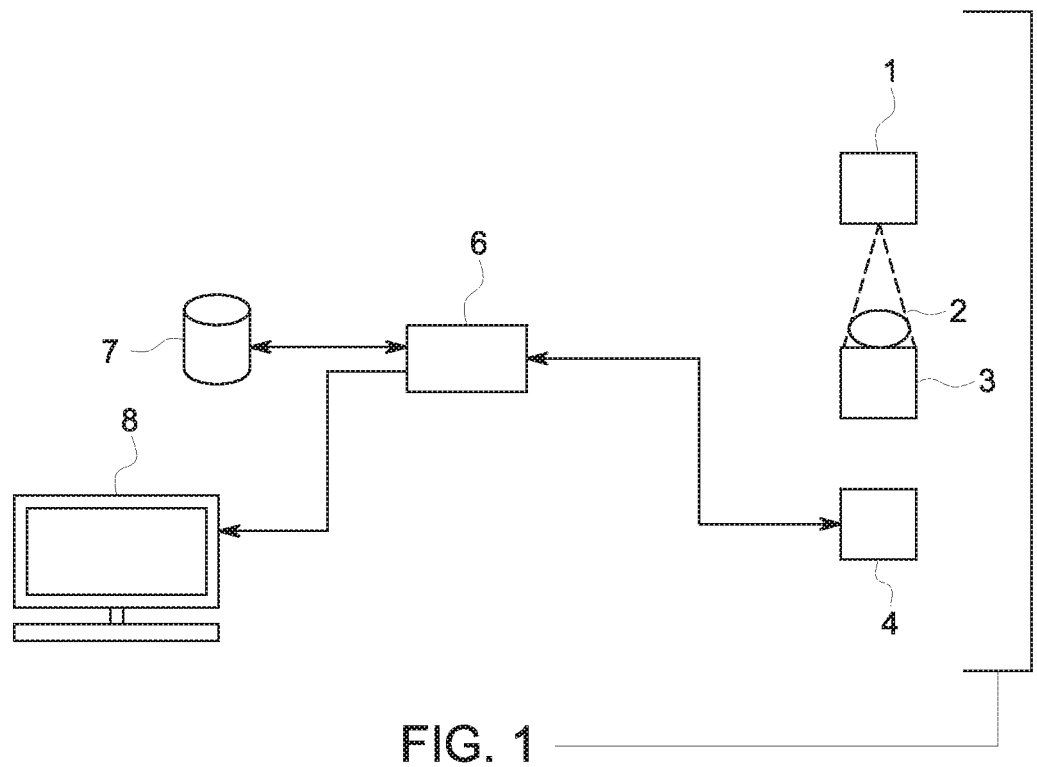
FIG. 1 is a schematic diagram of an x-ray imaging system.

Reference will be made below in detail to exemplary embodiments of the inventive subject matter, examples of which are illustrated in the accompanying drawings. Wherever possible, the same reference numerals used throughout the drawings refer to the same or like parts.

Although exemplary embodiments of the inventive subject matter are described with respect to medical x-ray detectors the current application applies to all types of x-ray detectors.

Referring to FIG. 1, X-ray imaging systems generally comprise any or all of an x-ray source 1 and an x-ray detector 4 configured to image an object or subject of interest 2, an object support 3, a display screen 8, and a processor 6 which may include a memory 7. An exemplary non-limiting embodiment of an imaging system is described in U.S. Pat. No. 8,563,938, which is commonly owned by General Electric Company and is incorporated by reference herein.

Figure 2:
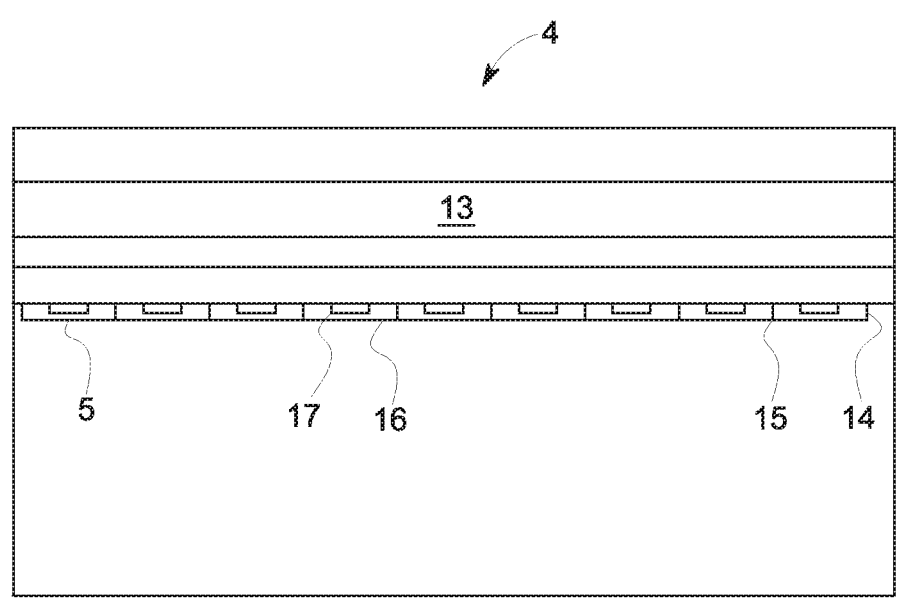
FIG. 2 is a cross-sectional schematic of an embodiment of an x-ray detector usable, for example, in the x-ray imaging system of FIG. 1.

X-ray detectors are devices configured to generate images by converting x-rays into light, detecting the amount of converted light and transmitting a corresponding electric signal to a computer or processor that will construct an image from the signal for viewing on an integrated or separate display. An exemplary non-limiting example of an X-ray detectors is depicted in FIG. 2. The x-ray detector 4 comprises a scintillator 13 and a pixel layer 14. The pixel layer 14 comprises multiple pixels 5, each pixel 5 having a nonlight sensitive area 16 and light sensitive area 17. The nonlight sensitive area 16 comprises one or more electronic components.

Figure 3:
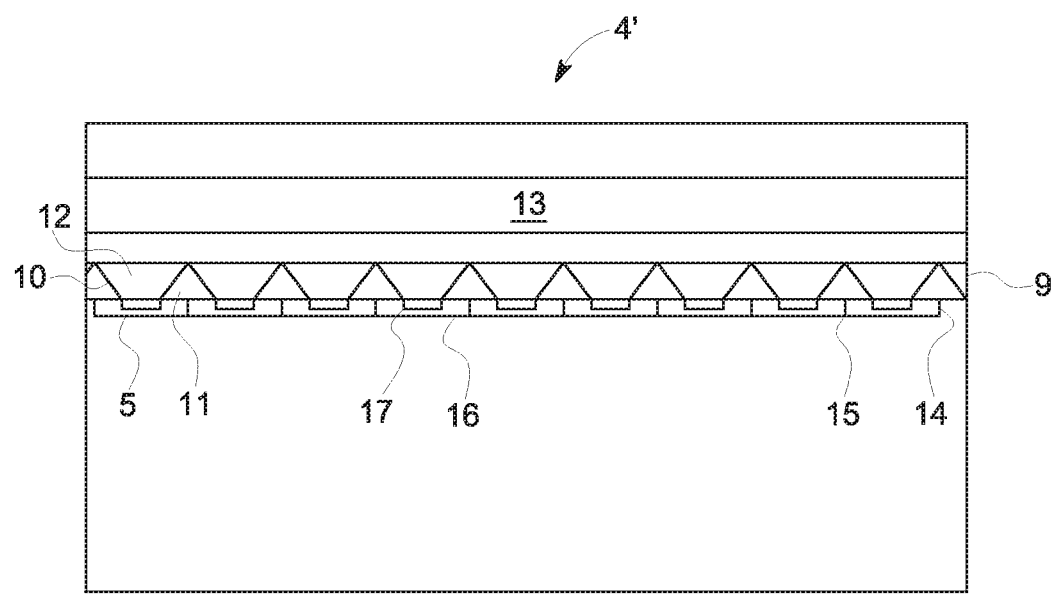
FIG. 3 is a cross-sectional schematic of an embodiment of the x-ray detector of FIG. 2 comprising a light redirection layer.

Now drawing attention to FIG. 3, a cross-section of an exemplary non-limiting embodiment of an x-ray detector is shown. The detector 4' comprises a scintillator 13, a light redirection layer 9, and pixel layer 14. In the depicted arrangement, the scintillator 13 is positioned closer to or biased toward the light redirection layer 9 in comparison to the pixel layer 14. This configuration enables the x-rays that have been turned into light in the scintillator 13 to pass through the redirection layer 9 before entering the pixels 14.

Figure 4:
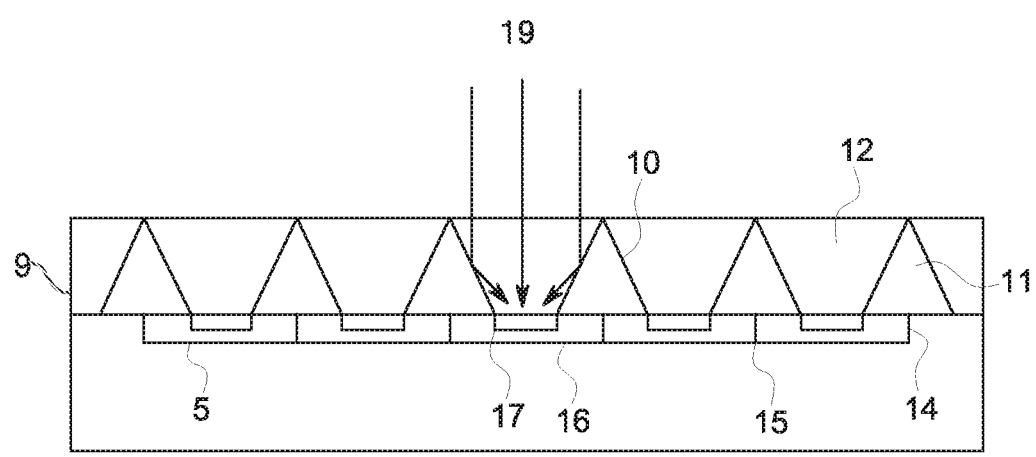
FIG. 4 is a cross-sectional schematic of an embodiment of the light redirection layer and pixel layer of the x-ray detector shown in FIG. 3.

Attention will now be drawn to the light redirection layer 9 (See FIGS. 3-6). The light redirection layer 9 is made up of one or more light redirection cells 18, shown in greater detail in FIG. 5. Each light redirecting cell 18 comprises, in part, a light reflection region 11 and a channel 12. The light redirecting cells 18 are generally defined by the shape of the pixels 5, including both the non-light sensitive area 16 and the light sensitive area 17. An exemplary non-limiting shape of the light redirection layer 9 is illustrated in FIG. 4. As shown, the top and the bottom of the light redirection layer are substantially flat, which enables the light redirection to rest substantially directly on the pixel layer, in an adjacent flush manner to minimize or eliminate space or gaps therebetween if desired.

The channels 12 of the light redirecting cells 18 are shaped to reflect light into the corresponding pixel(s) 5 (of the pixel layer 14) associated with each cell. As illustrated e.g. in FIG. 3, the channel defines an opening proximate to the scintillator layer 13. Additionally, the channel dimensionally tapers downward from the opening in a direction from the scintillator toward the pixel layer 14; in other words, the area of channel opening proximate to the scintillator layer is greater that the area of the channel opening proximate the pixel layer. To maximize the amount of light received by the pixel layer 14, the bottom opening of the channel is sized and/or configured to approximate the size and configuration of the light sensitive part of the pixel 17 and, in at least one exemplary non-limiting embodiment, is sized and/or configured to be substantially or exactly the size and/or configuration of the light sensitive area of the pixel 17. The channel 12 is made of any material allowing light to pass through said material to the pixels 5 of the pixel layer 14, including, but not limited to a solid, fluid, or combinations thereof.

The light reflective regions 11 is adjacent to the channel 12. The respective light reflective regions 11 are configured to cover (wholly or partially) the respective nonlight sensitive areas 16 of the pixels forming the pixel layer 14. Each light reflective region 11 is configured so that it tapers in a narrowing fashion in a direction from the pixel later toward the scintillator layer. The light reflective region 11 can be made of any material that reflects light including, but not limited to, a solid, fluid, or combinations thereof.

The channel 12 and the light reflective region 11 abut to form an interface 10. The interface 10 is created and defined by the meeting of the substances. The interface 10 creates an angle in relation to the light sensitive part of the pixel on the channel side of the light redirection cell. This angle is typically an obtuse angle, but other angles are contemplated. The interface 10 is the point or region at which the light 18 will be reflected and redirected into the pixel 14. In some embodiments, the reflective region comprises several layered substances 11a, 11b, 11c, (See FIG. 6) thus multiple interfaces may exist.

The light reflective region 11 may not be light reflective in its entirety. For example, the portion of the light reflective region 11 that creates the interface 10 with the channel 12 may, in at least one non-limiting embodiment, be the only reflective portion of the light reflective region 11, while the other portions(s) are not light reflective. Of course, the light reflective region 11 can be light reflective in its entirety, or reflective in certain portions other than or including the interface region noted above.

FIG. 4 is a cross section of the light redirection layer 9 in conjunction with the pixel layer 14. The pixel layer 14 comprises at least one pixel 5. Each pixel 5 comprises two areas; a light sensitive area or region 17 and a non-light sensitive area or region 16. The light sensitive area of each pixel 17 is the region where light is measured in order to be processed into an x-ray image.

In an exemplary non-limiting embodiment, the pixel layer 14 comprises multiple pixels. These pixels are placed end to end so that the non-light sensitive regions are adjacent to each other creating seams 15 of the pixels in the pixel layer 14. The seams 15 will leave missing data. As illustrated, the seams 15 are covered by the light reflective regions 11. This configuration allows the light 19 to be reflected off of the light reflective region 11 and be redirected into the light sensitive area 17 of the pixel 5. This configuration prevents light from being lost between pixels, in the seams 15 or in the non-light sensitive areas 16 of the pixels.

In FIG. 4 the pixels 5 are square-shaped or substantially square-shaped. It should be noted, however that the pixels 5 that form the pixel layer 14 do not need to be square or even substantially square for the light redirection layer 9 to redirect light into the light sensitive area of the pixel 17; accordingly, other known shapes can be implemented. Also, the light sensitive area 17 of the pixel does not need to be square or substantially square; it can be any shape. And the non-light sensitive area 16 does need to be square in perimeter; it can be any shape the designer desires.

Additionally, in the FIG. 4 depiction the non-light sensitive area 16 of the pixel 5 is approximately half of the light sensitive area 17 of the pixel. The non-light sensitive area 16 of the pixel is not limited to this ratio.

FIG. 4 shows in detail the light redirection layer 9. The light redirection layer 9 is made up of one or more light redirection cells 18 (See e.g. FIG. 5). The light redirecting cells 18 comprise the aforementioned channels 12 and light reflective regions 11. The light redirecting cells 18 are generally defined by the shape of the pixel 5, including both the light sensitive area 17 and the non-light sensitive area 16 of the pixel 5. The general shape of the light redirection layer 9 is illustrated in FIG. 4. The top and the bottom of the light redirection layers are substantially flat. The flat top and bottom allows the layer to rest on the pixel layer 14.

Each channel 12 of a respective light redirecting cell 18 is shaped to reflect light into the pixel 5. The channel has a wide opening closest to the scintillator. The channel tapers from the scintillator side to a smaller opening at the pixel side of the light redirection layer. The bottom opening of the channel is approximately (e.g. larger or smaller) the size the light sensitive part of the pixel 17 and in an at least embodiment, the bottom opening of the channel is the same size as the light sensitive area of the pixel 17. The channel 12 is made of a material that will allow light to pass through. Generally, this is a material that can be a fluid, solid, or any other light substance conducive to light passing through to the at least one pixel 5.

The light reflective region 11 is adjacent to the channel 12. The light reflective region 11 covers the nonlight sensitive area 16 of the pixel 5 and tapers in a direction from the pixel layer 14 toward the scintillator 13. The light reflective region 11 can be made of any material that reflects light including but not limited to any solid, fluid, or other substance.

The channel 12 and the light reflecting region 11 abut to form an interface 10. The interface 10 is created by the meeting of the substances. The interface 10 creates an angle in relation to the light sensitive part of the pixel on the channel side of the light redirection cell. This angle is an obtuse angle. The interface 10 is the region where the light 19 will be reflected and thus redirected into light sensitive area of the pixel 17. In some embodiments, the reflective region comprises several layered substances 11a, 11b, 11c, (See FIG. 6) thus multiple interfaces may exist.

In some embodiments, the light reflective region 11 may not be light reflective as a whole. The part of the light reflective region 11 that creates the interface 10 with the channel 12 may be the only part of the light reflective region 11 that is reflective. In this embodiment the other area of the light reflective region 11 need not be reflective.

Figure 5:
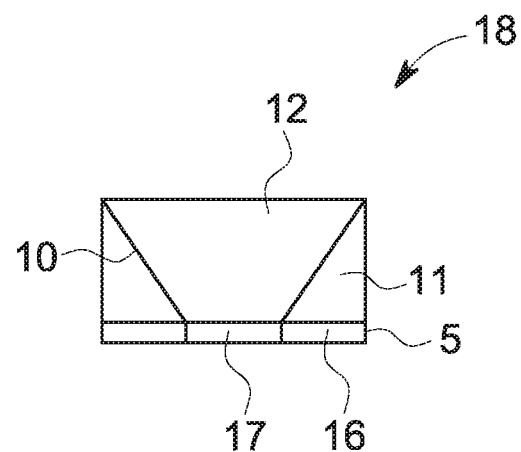
FIG. 5 is a cross-sectional schematic of an embodiment of a light redirection cell and corresponding pixel of the x-ray detector and elements shown in FIGS. 3-4.

FIG. 5 depicts a light redirecting cell 18. As illustrated, the light redirecting cell comprises a light reflective region 11 and a channel 12 with an interface 10 therebetween. The light reflective region 11 is configured to cover, in whole or in part, the non-light sensitive area 16 of the pixel 5, then tapers outwardly to the top of the light redirection layer 14 (i.e. tapers outwardly in a direction toward the scintillator (FIG. 3). The meeting of the light reflective region 11 and the channel 12 creates the interface 10 that is the first area of flection. This interface 10 is angled so light will travel toward the light sensitive area 17 of the pixel 5.

Figure 6:
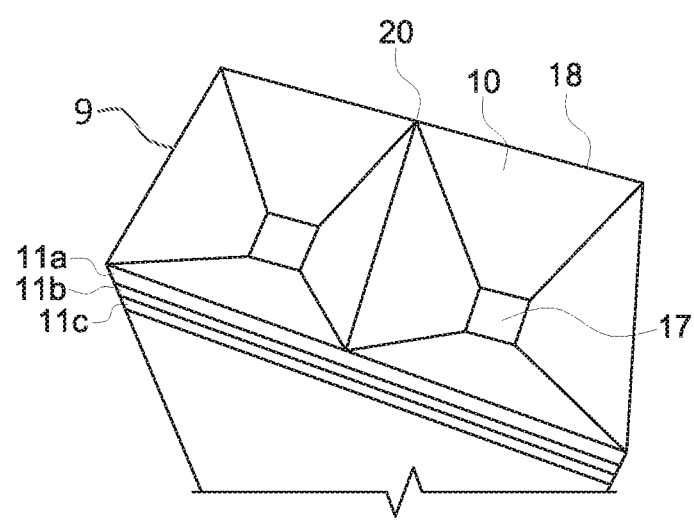
FIG. 6 is a top/side elevational view of the embodiment of the light redirection cell and pixel shown in FIG. 5.

In a non-limiting embodiment, an aerial view of the light redirection layer 9 is shown in FIG. 6. In this embodiment, the light redirection cells 18 can be viewed and the parameters of the light redirection cell can be seen, including the outer perimeters 20 of the light redirecting cells and the interface 10 between the channel 12 and the light reflective region 11. The shape of the cell is determined by the shape of the pixel (not shown) which it is reflecting light into. In this case, the pixel is square-shaped or substantially square-shaped, thus the light redirection cell 18 is the general shape of an inverted pyramid. In other embodiments, the pixel could take on a different shape, for example circular or triangular, thus the interface 10 and the perimeter or perimetric border 20 between the light redirection cells will be different in shape to coincide with the pixel shape.

In at least one non-limiting embodiment, depicted in FIG. 6, the light reflective region 11 can be made of multiple layers 11a, 11b, 11c. The first layer 11a being less reflective than the subsequent layers 11b, 11c. The subsequent layers 11b, 11c will reflect light that permeates the first layer 11a and enter into the light sensitive area 17 of the at least one pixel.

Figure 7:
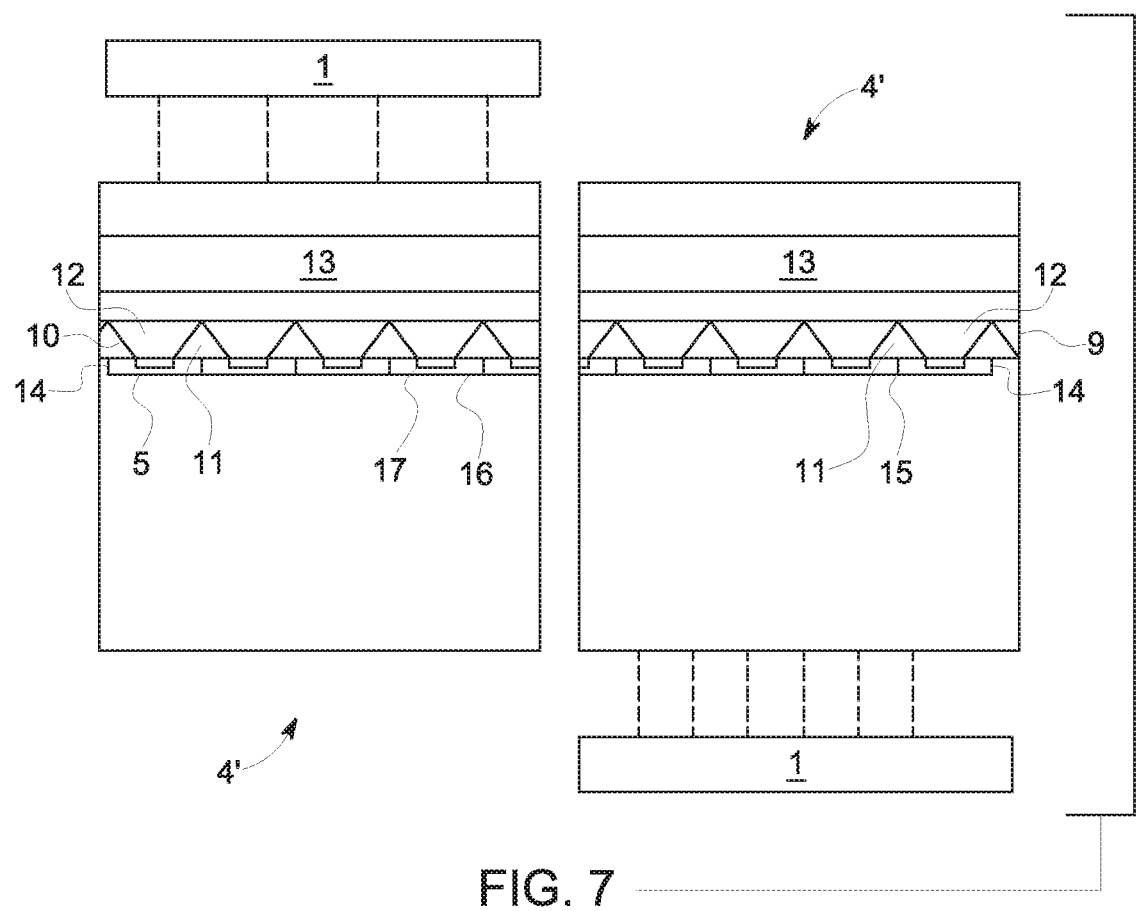
FIG. 7 is a schematic illustration of alternative arrangements of an x-ray source relative to the x-ray detector and elements shown in FIGS. 2-6.

FIG. 7 shows an embodiment of an arrangement of an x-ray source 1 relative to the elements of the x-ray detector 4'. Specifically, the arrangement of the x-ray source 1 to the scintillator 13 and the light redirection layer 9. In an embodiment, the scintillator 13 is located closer than the pixels 5 and pixel layer 14 than the x-ray source 1. In this embodiment, x-rays are emitted from the x-ray source 1 into the detector 4'. The x-rays are received in the scintillator 13 after passing through the light redirection layer 9 and the pixel layer 14. The scintillator 13 then converts the x-rays into light. The light then passes through the light redirection layer 9 into the pixel layer 14, more specifically into the light sensitive areas 17 of the pixels 5.

In another embodiment, shown in FIG. 7, an arrangement of an x-ray source 1 relative to the elements in a detector 4'. Here the detector 4' comprises a scintillator 13, the light redirection layer 9, and pixel layer 14. In this embodiment, the scintillator 13 is located closer to the x-ray source than the pixel layer 14. The x-rays are emitted from the x-ray source 1, into the detector 4'. The x-rays are received in the scintillator 13 before passing through the light redirection layer 9 and the pixels 14. The scintillator 13 then converts the x-rays into light. The light then passes through the light redirection layer 9 into the pixels.

Having thus described embodiments of the invention, attention will now be drawn to a non-limiting example of how the x-ray detector 4' operates within a typical x-ray imaging system. X-rays are emitted from the x-ray source 1 and pass through the subject of interest 2. The x-rays then enter the detector 4'. In the detector 4', the x-rays are converted into light by a scintillator 13 and then pass through a light redirection layer 9, See FIGS. 3-7.

As light enters the redirection layer 9 it enters a light redirection cell 18. Light is reflected off of the light reflective region 11 at the interface 10 (See FIG. 4) and is reflected at an angle toward the light sensitive area 17 of the pixels 5. The redirected light enters the light sensitive areas 17 of the pixels 5 and generates an electrical signal proportional to the amount of x-rays incident on a scintillator 13 area above it. Data from the pixels 5 is processed to form one or more x-ray images that are displayed on a display or screen 8. Additionally, the data may be stored in a memory unit 7. The present invention is not limited to the configuration shown, but rather, the configuration shown gives context to the present invention.

The configuration of the light redirecting cell creates advantages. For example, the light that would normally be lost between pixels is redirected an absorbed by a pixel. At least one other advantage is that the at least one pixel can have more electronics surrounding the light sensitive area of the at least on pixel. This will increase pixel sensitivity without losing light between pixels.

At least one advantage to the light redirection layer is that the pixel can be any shape. The pixel shape can be changed more easily because of the light redirection layer. The light redirection layer can be changed to accommodate different shapes. The light reflective region will taper toward the edge of the light sensitive area of the pixel covering the non-light sensitive area of the pixel no matter the shape of the non-light sensitive area and the light sensitive area.

At least one advantage to the light redirection layer is the ability to increase or decrease the non-light sensitive area of the pixel without losing light data in the non-light sensitive area. But, the light redirection layer will change according to the shape of the pixel.

Figure 8:
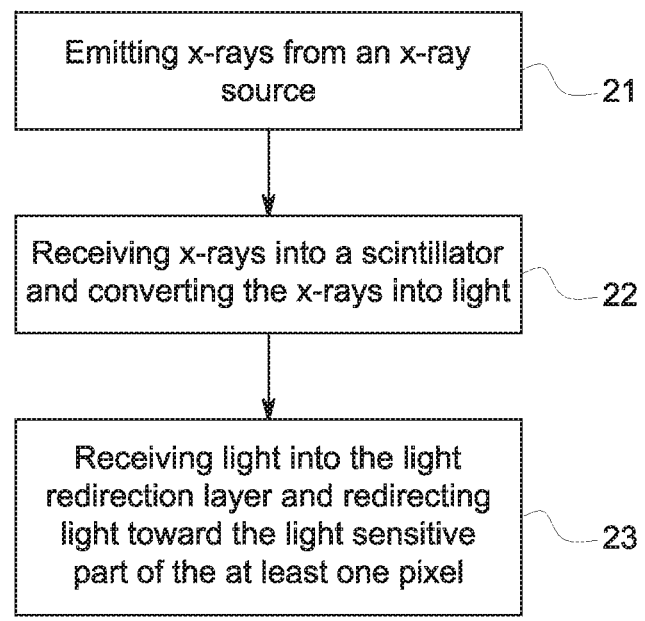
FIG. 8 is a schematic illustration of a method for redirecting light.

FIG. 8 shows a method of redirecting light from an x-ray detector scintillator toward the light sensitive area of a pixel.

At step 21, x-rays are emitted from the x-ray source. The x-rays that are emitted pass through the object that is to be imaged. The x-rays are either absorbed in to the object or the x-rays pass through the object.

At step 22, the x-rays, that have passed through the object, enter the x-ray detector and are received in the scintillator. The scintillator then converts the x-rays into light.

At step 23, the light enters into the light redirecting layer. The layer consists of light redirecting cells. The light redirecting cell redirects the light away from the nonlight sensitive part of the pixel and toward the light sensitive part of the pixel. The light redirection cell comprises a channel and a light reflective region. The channel directs the light toward the light sensitive part of the pixel and the light reflective region of the light redirection cell prevents the light from entering the non-light sensitive part of the pixel.

It is to be understood that the description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to those of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Additionally, the term pixel is used throughout the specification and should be interpreted to include one or more pixel. The term pixel is not restricted by any number because of the use of singular or multiple form.

This written description uses examples to disclose several embodiments of the inventive subject matter and also to enable any person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

What is claimed is:

1. An x-ray detector comprising:
   a scintillator configured to convert x-rays into light; and
   a light redirection layer configured to redirect the light from the scintillator to at least one pixel, the light redirection layer comprising at least one light redirecting cell comprising a channel and a light reflecting region, the channel arranged relative to the at least one pixel to direct incoming light away from a non-light sensitive part of the at least one pixel and toward the light sensitive part of the at least one pixel, wherein the light sensitive part and the non-light sensitive part of the at least one pixel directly contact each other along a same horizontal plane and the light reflecting region only covers the non-light sensitive part, and wherein the light reflecting region extends around an entirety of a perimeter of the light sensitive part of the at least one pixel;
   wherein the scintillator is separate from the light redirection layer, and an entirety of the scintillator is disposed over the light redirection layer.

2. The x-ray detector of claim 1, wherein the light reflecting region is adjacent to the channel to define a light reflecting interface tapering toward the at least one pixel.

3. The x-ray detector of claim 1, wherein the channel comprises a first substance and the light reflecting region comprises a second substance.

4. The x-ray detector of claim 3, wherein the first substance is a light permissive polymer and the second substance is a light reflecting polymer.

5. The x-ray detector of claim 3, wherein the first substance is a light permissive polymer and the second substance is a fluid.

6. The x-ray detector of claim 3, wherein the first substance is a fluid and the second substance is a light reflecting polymer.

7. The x-ray detector of claim 1, wherein the light reflecting region comprises a first layer disposed on top of a second layer, and the first layer is less reflective than the second layer.

8. A method of redirecting light comprising:
   emitting x-rays from an x-ray source;
   receiving the x-rays into a scintillator;
   converting the x-rays into light;
   receiving the light into a light redirection layer, wherein the light redirection layer comprises a light reflecting region; and
   redirecting the light in the light redirection layer away from a non-light sensitive part of at least one pixel and toward a light sensitive part of the at least one pixel, wherein the light sensitive part and the non-light sensitive part of the at least one pixel directly contact each other along a same horizontal plane and the light reflecting region only covers the non-light sensitive part, and wherein the light reflecting region extends around an entirety of a perimeter of the light sensitive part of the at least one pixel;
   wherein the scintillator is separate from the light redirection layer, and an entirety of the scintillator is disposed over the light redirection layer.

9. The method of claim 8, wherein the light redirection layer comprises a channel and the light reflecting region is adjacent to the channel to define a light reflecting interface tapering toward the at least one pixel.

10. The method of claim 8, wherein the scintillator receives the x-rays from a first side of the scintillator that is facing the x-ray source, converts the x-rays to light, and emits the light from a second side of the scintillator that is not facing the x-ray source into the light redirection layer.

11. The method of claim 8, wherein the scintillator receives x-rays through the light redirection layer into the first side of the scintillator that is facing the x-ray source, converts the x-rays to light, and emits the light from the first side of the scintillator that is facing the x-ray source into the light redirection layer.

12. The method of claim 8, wherein the light reflecting region comprises a first layer disposed on top of a second layer, and the first layer is less reflective than the second layer.

13. A x-ray system comprising:
an x-ray source configured to generate x-rays; and
an x-ray receptor or detector comprising:
a scintillator configured to convert x-rays into light; and
a light redirection layer configured to redirect the light from the scintillator to at least one pixel, the light redirection layer comprising at least one light redirecting cell comprising a channel and a light reflecting region, the channel arranged relative to the at least one pixel to direct incoming light away from a non-light sensitive part of the at least one pixel and toward a light sensitive part of the at least one pixel, wherein the light sensitive part and the non-light sensitive part of the at least one pixel directly contact each other along a same horizontal plane and the light reflecting region only covers the non-light sensitive part, and wherein the light reflecting region extends around an entirety of a perimeter of the light sensitive part of the at least one pixel;
wherein the scintillator is separate from the light redirection layer, and an entirety of the scintillator is disposed over the light redirection layer.

14. The x-ray system of claim 13, wherein the light reflecting region is adjacent to the channel to define a light reflecting interface tapering toward the at least one pixel.

15. The x-ray system of claim 13, wherein the channel comprises a first substance and the light reflecting region comprises a second substance.

16. The x-ray system of claim 15, wherein the first substance is a light permissive polymer and the second substance is a light reflecting polymer.

17. The x-ray system of claim 15, wherein the first substance is a light permissive polymer and the second substance is a fluid.

18. The x-ray system of claim 15, wherein the first substance is a fluid and the second substance is a light reflecting polymer.

19. The x-ray system of claim 13, wherein the light reflecting region comprises a first layer disposed on top of a second layer, and the first layer is less reflective than the second layer.

* * * * *